United States Patent
Determan et al.

(10) Patent No.: US 10,370,571 B2
(45) Date of Patent: Aug. 6, 2019

(54) SILICONE GEL ADHESIVE WITH HYDROPHILLIC AND ANTIMICROBIAL PROPERTIES

(71) Applicant: 3M INNOVATIVE PROPERTIES COMPANY, St. Paul, MN (US)

(72) Inventors: Michael D. Determan, Mahtomedi, MN (US); Kiu-Yuen Tse, Woodbury, MN (US); Joon Chatterjee, Bloomington, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 700 days.

(21) Appl. No.: 14/648,633

(22) PCT Filed: Mar. 13, 2013

(86) PCT No.: PCT/US2013/030670
§ 371 (c)(1),
(2) Date: May 29, 2015

(87) PCT Pub. No.: WO2014/088622
PCT Pub. Date: Jun. 12, 2014

(65) Prior Publication Data
US 2015/0299542 A1    Oct. 22, 2015

Related U.S. Application Data

(60) Provisional application No. 61/734,653, filed on Dec. 7, 2012.

(51) Int. Cl.
| | | |
|---|---|---|
| *C09J 183/02* | (2006.01) | |
| *C09J 183/04* | (2006.01) | |
| *A61L 31/06* | (2006.01) | |
| *A61L 31/16* | (2006.01) | |
| *A61L 15/46* | (2006.01) | |
| *A61L 15/58* | (2006.01) | |

(Continued)

(52) U.S. Cl.
CPC ............ *C09J 183/02* (2013.01); *A61L 15/46* (2013.01); *A61L 15/58* (2013.01);
(Continued)

(58) Field of Classification Search
CPC ......... A61L 15/46; A61L 15/58; C08K 5/101; C09J 183/02; C09J 183/04
(Continued)

(56) References Cited

U.S. PATENT DOCUMENTS

| | | |
|---|---|---|
| 6,746,765 B1 | 6/2004 | Fattman |
| 8,124,675 B2 | 2/2012 | Bougherara |

(Continued)

FOREIGN PATENT DOCUMENTS

| | | |
|---|---|---|
| GB | 1088992 | 10/1967 |
| JP | 2006-070122 | 3/2006 |

(Continued)

OTHER PUBLICATIONS

International Search Report for PCT International Application No. PCT/US2013/030670 dated Aug. 9, 2013, 4 pages.

*Primary Examiner* — Vincent Tatesure
(74) *Attorney, Agent, or Firm* — Jean A. Lown

(57) ABSTRACT

Adhesive compositions are provided that include a crosslinked silicone gel, a hydrophilic component dispersed in the silicone gel, and an antimicrobial agent dispersed in the silicone gel. The adhesive composition is readily applied to (and removed from) skin, and has desirable hydrophilic and antimicrobial properties. Advantageously, the hydrophilic component in the crosslinked silicone gel is not readily extractable (e.g., into a pH 7 buffer). Surprisingly, the combination of hydrophilic component with antimicrobial agent in the crosslinked silicone gel can provide a synergistic level of antimicrobial activity.

20 Claims, 1 Drawing Sheet

(51) Int. Cl.
*A61L 24/00* (2006.01)
*A61L 24/04* (2006.01)
*C08K 5/101* (2006.01)
*C08L 9/02* (2006.01)

(52) U.S. Cl.
CPC ......... *A61L 24/0015* (2013.01); *A61L 24/046* (2013.01); *A61L 31/06* (2013.01); *A61L 31/16* (2013.01); *C08K 5/101* (2013.01); *C08L 9/02* (2013.01); *C09J 183/04* (2013.01); *A61L 2300/102* (2013.01); *A61L 2300/104* (2013.01); *A61L 2300/404* (2013.01)

(58) Field of Classification Search
USPC .......................................................... 442/149
See application file for complete search history.

(56) References Cited

U.S. PATENT DOCUMENTS

| | | |
|---|---|---|
| 9,278,155 B2 | 3/2016 | Asmus |
| 2007/0179461 A1 | 8/2007 | Sambasivam |
| 2011/0206923 A1 | 8/2011 | Liu |
| 2011/0206924 A1 | 8/2011 | Liu |
| 2011/0212325 A1 * | 9/2011 | Determan ............... A61L 15/58 428/332 |
| 2012/0037038 A1 * | 2/2012 | Rajaiah ................ A61K 6/0023 106/35 |
| 2013/0101633 A1 | 4/2013 | Löwenhielm |
| 2013/0295372 A1 | 11/2013 | Liu |

FOREIGN PATENT DOCUMENTS

| | | |
|---|---|---|
| WO | WO 2005-102403 | 11/2005 |
| WO | WO 2006/028612 | 3/2006 |
| WO | WO 2008-057155 | 5/2008 |
| WO | WO 2010-056544 | 5/2010 |
| WO | WO 2011-129759 | 10/2011 |
| WO | WO 2013-025579 | 2/2013 |
| WO | WO-2013056045 A1 * | 4/2013 ............ C09J 183/06 |
| WO | WO 2013-090191 | 6/2013 |

* cited by examiner

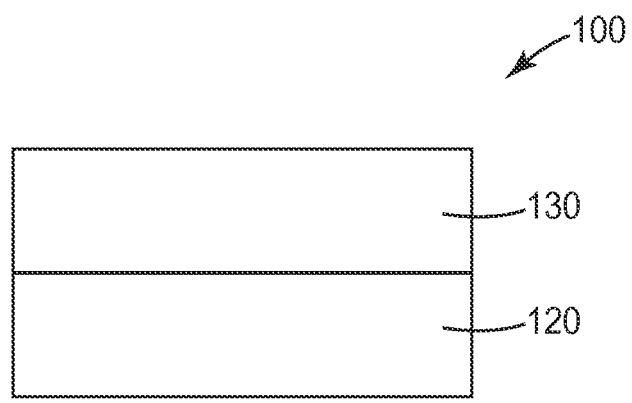

US 10,370,571 B2

SILICONE GEL ADHESIVE WITH HYDROPHILLIC AND ANTIMICROBIAL PROPERTIES

TECHNICAL FIELD

The present disclosure relates to hydrophilic silicone gel adhesives and more specifically to crosslinked hydrophilic silicone gel adhesives that are made by methods including electron beam or gamma ray curing.

BACKGROUND

The application of pressure sensitive adhesives (PSAs), including silicone pressure sensitive adhesives, for adhering to skin is known in the art and many examples are commercially available. However, some properties of PSAs limit their application for adhesion to skin. For instance, skin damage may result during the removal of a PSA that exhibits too high a level of adhesive strength. Alternatively, if the adhesive strength is reduced, the PSA may lack sufficient holding power to be useful or will lose sufficient tackiness at room temperature to be useful. Additionally, PSAs that are relatively rigid or non-conformable compared to skin typically result in considerable patient discomfort during use. Also, even adhesives that have a measured low peel adhesion to skin may cause discomfort during removal, e.g., if the adhesive becomes entangled with hair.

SUMMARY

Adhesive compositions of the present disclosure include a crosslinked silicone gel, a hydrophilic component dispersed in the silicone gel, and an antimicrobial agent dispersed in the silicone gel. The adhesive composition is readily applied to (and removed from) skin, and has desirable hydrophilic and antimicrobial properties. Advantageously, the hydrophilic component in the crosslinked silicone gel is not readily extractable (e.g., into a pH 7 buffer). Surprisingly, the combination of hydrophilic component with antimicrobial agent in the crosslinked silicone gel can provide a synergistic level of antimicrobial activity.

In a first aspect, the present disclosure provides an adhesive composition that includes a silicone gel having a crosslinked poly(diorganosiloxane). The crosslinked poly(diorganosiloxane) has terminal groups of formula —O—Si($R^1$)($R^2$)$_2$ wherein $R^1$ is hydroxyl, alkyl, or aryl and each $R^2$ is independently alkyl or aryl. A hydrophilic component is dispersed in the silicone gel. The hydrophilic component has at least one carbohydrate having at least 3 hydroxyl groups, carbohydrate derivative having at least 3 hydroxyl groups, or a combination thereof. An antimicrobial agent is also dispersed in the silicone gel. The antimicrobial agent can include elemental copper, elemental silver, a copper-containing compound, a silver-containing compound, or a combination thereof. Less than 10 weight percent of the hydrophilic component is extractable from the adhesive composition into a phosphate buffer saline solution at pH 7 within 24 hours at room temperature.

In a second aspect, the present disclosure provides an article having a substrate and a layer of the adhesive composition of the first aspect adhered to the substrate. Useful articles can include, for example, medical articles such as tapes, wound dressings, surgical drapes, IV site dressings, a prosthesis, an ostomy or stoma pouch, a buccal patch, or a transdermal patch.

The above summary of the present disclosure is not intended to describe each embodiment of the present invention. The details of one or more embodiments of the invention are also set forth in the description below. Other features, objects, and advantages of the invention will be apparent from the description and from the claims.

BRIEF DESCRIPTION OF DRAWINGS

FIG. 1 illustrates an article according to some embodiments of the present disclosure.

DETAILED DESCRIPTION

In some uses of adhesive compositions (e.g., for medical dressings), there is a need to manage moisture that may be present at an adhesion site. Inclusion of a hydrophilic component in an adhesive composition can enhance the ability of the adhesive composition to adhere when moisture is present. Preferably, the hydrophilic component has a low level of extractability from the adhesive composition, and this is particularly advantageous in medical uses of the adhesive composition. It is also often desirable that the hydrophilic component not be readily extracted from the adhesive composition by the moisture (e.g., at a wound site). Additionally, it is often desirable to include an antimicrobial agent in the adhesive composition, and preferably the combination of hydrophilic component and antimicrobial agent in the adhesive composition can result in a synergistic enhancement of antimicrobial properties at the adhesion site.

As used herein, "hydrophilic" is used to describe materials that can be wet by water, or by aqueous solutions or suspensions (e.g., wound exudates). In certain preferred embodiments, articles including adhesive compositions of the present disclosure can be sufficiently hydrophilic to absorb at least 1 gram of water per 1 gram of the article. "Hydrophilic component" and "hydrophilic additive" are used synonymously throughout the present disclosure.

Silicone gels are part of a class of materials typically known as filler-free silicone elastomers. Typical fillers that are absent in these materials are pyrogenic and precipitated silicas, silica aero-gels and carbon blacks. It is well known that covalent crosslinking of pure polysiloxanes yields elastomers whose mechanical strength is very low compared with that of organic elastomers. Silicone gels are typically understood to be under-crosslinked PDMS networks that exhibit greater extensibility, tack and a gelatinous consistency relative to fully crosslinked filler-free silicone elastomers. These physical properties result from the presence of free polysiloxane chains or polysiloxane chains that are covalently linked to the PDMS network only at one point. Under-crosslinked filler free silicone elastomers, or silicone gels, exhibit pronounced viscoelastic behavior. Silicone gels are highly dissipative under deformation, resulting in pronounced damping, self-healing and resiliency properties. Another key characteristic of silicone gels is a naturally tacky surface. This natural adhesion allows gels to gain a degree of physical adhesion to most common surfaces without the need for primers. Silicone gels retain much of the stress relief and self-healing qualities of a liquid while providing the dimensional stability of an elastomer. Silicone gels have been used to isolate circuits from the harmful effects of moisture and other contaminants and provide electrical insulation for high voltages. Additionally, silicone gels are used in healthcare applications, such as adhesive tapes and dressings, where very gentle removal from skin is desired. Silicone gels are softer than silicone pressure sensitive adhesives (PSAs), resulting in less discomfort when adhered to, and subsequently removed from, skin. The combination of moderate adhesive strength and tack make silicone gels suitable for many skin adhesive applications.

Generally, adhesive compositions of the present disclosure include a silicone gel that has a crosslinked poly (diorganosiloxane). The crosslinked poly(diorganosiloxane) has terminal end groups of Formula 1:

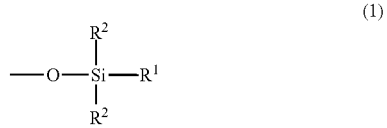

(1)

where $R^1$ is hydroxyl, alkyl, or aryl, and each $R^2$ is independently alkyl or aryl. The poly(diorganosiloxanes) have a poly(siloxane) backbone. In some embodiments, the poly (diorganosiloxane) can be a linear material described by Formula 2, illustrating a siloxane backbone with aliphatic and/or aromatic substituents:

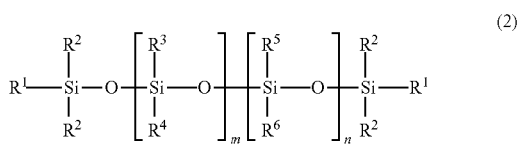

(2)

wherein each $R^1$ is independently hydroxyl, alkyl, or aryl, and wherein each $R^2$, $R^3$, $R^4$, $R^5$, and $R^6$ is independently alkyl or aryl, and m and n are integers, and at least one of m or n is not zero. An alkyl group can include 1 to about 20 carbon atoms, and an aryl group typically includes 6 to 10 carbon atoms. In some embodiments, one or more of the alkyl or aryl groups may contain a halogen substituent, e.g., fluorine. For example, in some embodiments, one or more of the alkyl groups may be —$CH_2CH_2C_4F_9$.

In some embodiments, $R^1$ and $R^2$ are methyl groups, i.e., the poly(diorganosiloxane) material is terminated by trimethylsiloxy groups. In some further embodiments, $R^3$ and $R^4$ are alkyl groups and n is zero, and the material is referred to as a poly(dialkylsiloxane). When the alkyl groups in a poly(dialkylsiloxane) are methyl groups, the material is a poly(dimethylsiloxane) ("PDMS"). The poly(diorganosiloxane) can be, for example, a PDMS having —$Si(OH)(CH_3)_2$ or —$Si(CH_3)_3$ terminal groups. In some embodiments, $R^3$ is an alkyl group, $R^4$ is an aryl group, and n is zero, i.e., the material is a poly(alkylarylsiloxane). In some embodiments, $R^3$ is methyl group and $R^4$ is a phenyl group, i.e., the material is poly(methylphenylsiloxane). In some embodiments, $R^3$ and $R^4$ are alkyl groups and $R^5$ and $R^6$ are aryl groups, i.e., the material is a poly(dialkyldiarylsiloxane). In some embodiments, $R^3$ and $R^4$ are methyl groups, and $R^5$ and $R^6$ are phenyl groups, i.e., the material is poly(dimethyldiphenylsiloxane).

In some embodiments, the poly(diorganosiloxane) materials can be a branched material described by Formula 3, illustrating a siloxane backbone that includes at least one linear or branched siloxane substituent among substituents $R^7$, $R^8$, $R^9$, and $R^{10}$:

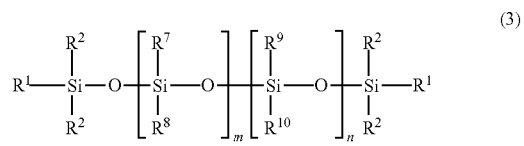

(3)

wherein each $R^1$ is independently hydroxyl, alkyl, or aryl, each $R^2$ is independently alkyl or aryl, and at least one of $R^7$, $R^8$, $R^9$, and $R^{10}$ is a linear or branched siloxane with alkyl or aryl (optionally including halogenated alkyl or aryl) substituents, the linear or branched siloxane having the terminal end group of Formula 1, and m and n are integers, and at least one of m or n is not zero. Any remaining R-groups among $R^7$, $R^8$, $R^9$, and $R^{10}$ in Formula 3 (i.e., if not a linear or branched siloxane) are independently alkyl or aryl (optionally including halogenated alkyl or aryl). Alkyl and aryl for Formula 3 are as defined for Formula 2.

As used herein, "nonfunctional groups" are either alkyl or aryl groups consisting of carbon, hydrogen, and in some embodiments, halogen (e.g., fluorine) atoms. As used herein, a "nonfunctionalized poly(diorganosiloxane) material" is one in which the $R^1$, $R^2$, $R^3$, $R^4$, $R^5$, $R^6$, $R^7$, $R^8$, $R^9$, and $R^{10}$ groups are nonfunctional groups.

Generally, the crosslinked poly(diorganosiloxane) materials of the present disclosure can be formed from either silanol-terminated or non-functional poly(diorganosiloxane) materials. These silicone gel adhesives have excellent wetting characteristics, due to the very low glass transition temperature (Tg) and modulus of the crosslinked poly (diorganosiloxane) network. Rheologically, these gels exhibit similar storage moduli at bond making and bond breaking time scales, resulting in relatively low to moderate forces being required to debond the adhesive by peeling. This results in minimal to no skin trauma upon removal. Additionally, the elastic nature of the crosslinked gel prevents flow of the adhesive around hair during skin wear, further reducing the instances of pain during removal.

Generally, the silicone materials may be oils, fluids, gums, elastomers, or resins (e.g., friable solid resins). Generally, lower molecular weight, lower viscosity materials are referred to as fluids or oils, while higher molecular weight, higher viscosity materials are referred to as gums; however, there is no sharp distinction between these terms. Elastomers and resins have even higher molecular weights that gums, and typically do not flow. As used herein, the terms "fluid" and "oil" refer to materials having a dynamic viscosity at 25° C. of no greater than 1,000,000 mPa·sec (e.g., less than 600,000 mPa·sec), while materials having a dynamic viscosity at 25° C. of greater than 1,000,000 mPa·sec (e.g., at least 10,000,000 mPa·sec) are referred to as "gums".

Suitable examples of poly(diorganosiloxane) materials useful for preparation of adhesive compositions of the present disclosure are commercially available, including a trimethylsilyl-terminated poly(dimethylsiloxane) silicone fluid available under the trade designation "AK 60000" from Wacker Chemical Corp. (Adrian, Mich.), a two-part soft skin adhesive available under the trade designation "DOW CORNING MG 7-9900" from Dow Corning (Midland, Mich.), and a poly(diorganosiloxane) fluid with silanol end groups available under the trade designation "OHX-4070" from Xiameter (Midland, Mich.).

Adhesive compositions of the present disclosure include a hydrophilic component dispersed in the silicone gel. The hydrophilic component aides in managing moisture that may be present at an adhesion site, by absorbing moisture. The hydrophilic component can be a carbohydrate having at least 3 hydroxyl groups, a carbohydrate derivative having at least 3 hydroxyl groups, or a combination thereof.

Examples of carbohydrates having at least 3 hydroxyl groups can include saccharides, including monosaccharides, disaccharides, trisaccharides, polysaccharides, or combinations thereof. Some other examples of carbohydrates having at least 3 hydroxyl groups can include cellulosic materials.

Examples of carbohydrate derivatives having at least 3 hydroxyl groups can include reduced saccharides (e.g., reduced monosaccharides, reduced disaccharides, reduced trisaccharides, reduced polysaccharides, and including sugar alcohols such as mannitol, sorbitol, glycerol), partially alkoxylated carbohydrates, partially alkoxylated reduced saccharides, carboxyalkylated carbohydrates (e.g., carboxymethylated carbohydrates), or combinations thereof. Some other examples of alkoxylated carbohydrate derivatives having at least 3 hydroxyl groups can include alkoxylated or carboxyalkylated cellulosic materials.

Examples of alkoxylated carbohydrate derivatives can include methoxylated or ethoxylated derivatives, ether-type alkoxylated derivatives of carbohydrates (including, e.g., ethyl 2-hydroxyethyl or methyl 2-hydroxyethyl derivatives), or combinations of any of the foregoing alkoxylated derivatives.

Some other examples of carbohydrate derivatives having at least 3 hydroxyl groups can include ionic carbohydrate polymers that are based on naturally occurring polysaccharides (e.g., sodium Carboxymethylcellulose) and other modified cellulose derivatives (e.g., cellulose ethyl ether; cellulose ethyl hydroxyethyl ether; cellulose hydroxyethyl ether; cellulose methyl hydroxyethyl ether), aliginic acid, sodium alginate, guar gum; pullulan, pectin, arabic gum, and similar materials derived from carrageenans (from seaweed), pectins (from plant extracts) and xanthan (from microbial fermentation process). Of the ionic carbohydrate polymers, sodium alginate and carboxymethyl cellulose are most preferred.

In some embodiments, adhesive compositions of the present disclosure include the hydrophilic component in an amount of at least 5 weight percent, at least 10 weight percent, or even at least 20 weight percent, relative to a total weight of the adhesive composition. In some embodiments, adhesive compositions of the present disclosure include the hydrophilic component in an amount of up to 50 weight percent, up to 40 weight percent, or even up to 35 weight percent, relative to a total weight of the adhesive composition. In some embodiments, adhesive compositions of the present disclosure include the hydrophilic component in a range from 5 weight percent to 50 weight percent, from 10 weight percent to 40 weight percent, or even from 20 weight percent to 35 weight percent, relative to a total weight of the adhesive composition.

The hydrophilic component of the present disclosure can absorb moisture (e.g., water). In some instances, an adhesive composition of the present disclosure can absorb water in amount (by weight) that is at least 100% of an initial weight of the adhesive composition (see Examples section).

Adhesive compositions of the present disclosure include an antimicrobial agent dispersed in the silicone gel. Suitable antimicrobial agents can include elemental copper, elemental silver, a copper-containing compound, a silver-containing compound, or a combination thereof. In some instances it is preferable that the antimicrobial agent be a salt, for example, a copper salt, a silver salt, or a combination thereof.

In some embodiments, adhesive compositions of the present disclosure can include the antimicrobial agent in an amount of at least 0.1 weight percent, at least 0.5 weight percent, or even at least 1.0 weight percent, relative to a total weight of the adhesive composition. In some embodiments, the antimicrobial agent is present in an amount of up to 20 weight percent, up to 10 weight percent, or even up to 5.0 weight percent, relative to a total weight of the adhesive composition. In some embodiments, the amount of antimicrobial agent is in a range from 0.1 weight percent to 20 weight percent, from 0.5 to 10 weight percent, or even from 1.0 to 5.0 weight percent, relative to a total weight of the adhesive composition.

In some embodiments, adhesive compositions of the present disclosure can include 35 to 95 weight percent silicone gel, 5 to 50 weight percent hydrophilic component, and 0.1 to 20 weight percent antimicrobial agent, wherein each amount is based on a total weight of the adhesive composition. More preferably, the adhesive composition can include 40 to 80 weight percent silicone gel, 10 to 40 weight percent hydrophilic component, and 0.5 to 10 weight percent antimicrobial agent, wherein each amount is based on a total weight of the adhesive composition. Even more preferably, the adhesive composition can include 45 to 60 weight percent silicone gel, 20 to 35 weight percent hydrophilic component, and 1 to 5 weight percent antimicrobial agent, wherein each amount is based on a total weight of the adhesive composition. The amounts of silicone gel, hydrophilic component, and antimicrobial agent can be selected to have any value within these ranges, with allowance for any of the optional additives described below, to obtain a total weight of the adhesive composition.

The adhesive compositions of the present disclosure may be prepared by combining one or more poly(diorganosiloxane) materials (e.g., silicone oils or fluids) with the hydrophilic component and antimicrobial agent, coating the resulting combination, and curing using electron beam (E-beam) or gamma radiation. A tackifying resin can optionally be included, to modify adhesive properties of the adhesive compositions.

If included, generally, any known tackifying resin may be used, for example, silicate tackifying resins may be used. The tackifying resin is usually selected to be miscible with the silicone gel. In some exemplary adhesive compositions, a plurality of silicate tackifying resins can be used to achieve desired performance.

Suitable silicate tackifying resins include those resins composed of the following structural units M (i.e., monovalent $R'_3SiO_{1/2}$ units), D (i.e., divalent $R'_2SiO_{2/2}$ units), T (i.e., trivalent $R'SiO_{3/2}$ units), and Q (i.e., quaternary $SiO_{4/2}$ units), and combinations thereof. Typical exemplary silicate resins include MQ silicate tackifying resins, MQD silicate tackifying resins, and MQT silicate tackifying resins. These silicate tackifying resins usually have a number average molecular weight in the range of 100 to 50,000-gm/mole, e.g., 500 to 15,000 gm/mole and generally R' groups are methyl groups.

MQ silicate tackifying resins are copolymeric resins where each M unit is bonded to a Q unit, and each Q unit is bonded to at least one other Q unit. Some of the Q units are bonded to only other Q units. However, some Q units are bonded to hydroxyl radicals resulting in $HOSiO_{3/2}$ units (i.e., "$T^{OH}$" units), thereby accounting for some silicon-bonded hydroxyl content of the silicate tackifying resin.

The level of silicon bonded hydroxyl groups (i.e., silanol) on the MQ resin may be selected from to no greater than 5 weight percent, no greater than 3 weight percent, or even no greater than 1.5 weight percent based on the weight of the silicate tackifying resin.

MQD silicone tackifying resins are terpolymers having M, Q and D units. MQT silicate tackifying resins are terpolymers having M, Q and T units.

Suitable silicate tackifying resins are commercially available from sources such as Dow Corning (e.g., DC 2-7066), Momentive Performance Materials (e.g., SR545 and SR1000), and Wacker Chemie AG (e.g., BELSIL TMS-803).

In some embodiments, adhesive compositions of the present disclosure include 35 to 95 weight percent silicone gel, 5 to 50 weight percent hydrophilic component, 0.1 to 20 weight percent antimicrobial agent, and 0.1 to 59.9 weight percent tackifier, wherein each amount is based on a total weight of the adhesive composition. More preferably, the adhesive composition can include 40 to 80 weight percent silicone gel, 10 to 40 weight percent hydrophilic component, 0.5 to 10 weight percent antimicrobial agent, and 5 to 49.5 weight percent tackifier, wherein each amount is based on a total weight of the adhesive composition. Even more preferably, the adhesive composition can include 45 to 60 weight percent silicone gel, 20 to 35 weight percent hydrophilic component, 1 to 5 weight percent antimicrobial agent, and 10 to 34 weight percent tackifier, wherein each amount is based on a total weight of the adhesive composition.

In some embodiments, the adhesives optionally include any of a variety of known fillers and additives including, but not limited to, fumed silica, pigments, dyes or fragrances.

The poly(diorganosiloxane) material, the hydrophilic component, the antimicrobial agent, the tackifying resin (if present), and any optional additives may be combined by any of a wide variety of known means prior to being coated and cured. For example, in some embodiments, the various components may be pre-blended using common equipment such as mixers, blenders, mills, extruders, and the like.

In some embodiments, the materials may be dissolved in a solvent, coated, and dried prior to curing. In some embodiments, solventless compounding and coating processes may be used. In some embodiments, solventless coating may occur at about room temperature. For example, in some embodiments, the materials may have kinematic viscosity of no greater than 100,000 centistokes (cSt), e.g., no greater than 50,000 cSt. However, in some embodiments, hot melt coating processes such as extrusion may be used, e.g., to reduce the viscosity of higher molecular weight materials to values more suitable for coating. The various components may be added together, in various combinations or individually, through one or more separate ports of an extruder, blended (e.g., melt mixed) within the extruder, and extruded to form the hot melt coated composition.

Regardless of how it is formed, the coated compositions are radiation cured. In some embodiments, coating may be cured through exposure to E-beam radiation. In some embodiments, the coating may be cured through exposure to gamma radiation. In some embodiments, a combination of electron beam curing and gamma ray curing may be used. For example, in some embodiments, the coating may be partially cured by exposure to electron beam radiation. Subsequently, the coating may be further cured by gamma radiation.

A variety of procedures for E-beam and gamma ray curing are well-known. The cure depends on the specific equipment used, and those skilled in the art can define a dose calibration model for the specific equipment, geometry, and line speed, as well as other well understood process parameters.

Commercially available electron beam generating equipment is readily available. For the examples described herein, the radiation processing was performed on a Model CB-300 electron beam generating apparatus (available from Energy Sciences, Inc. (Wilmington, Mass.). Generally, a support film (e.g., polyester terephthalate support film) runs through a chamber. In some embodiments, a sample of uncured material with a liner (e.g., a fluorosilicone release liner) on both sides ("closed face") may be attached to the support film and conveyed at a fixed speed of about 6.1 meters/min (20 feet/min). In some embodiments, a sample of the uncured material may be applied to one liner, with no liner on the opposite surface ("open face"). Generally, the chamber is inerted (e.g., the oxygen-containing room air is replaced with an inert gas, e.g., nitrogen) while the samples are e-beam cured, particularly when open-face curing.

The uncured material may be exposed to E-beam radiation from one side through the release liner. For making a single layer laminating adhesive type tape, a single pass through the electron beam may be sufficient. Thicker samples, may exhibit a cure gradient through the cross section of the adhesive so that it may be desirable to expose the uncured material to electron beam radiation from both sides.

Commercially available gamma radiation equipment includes equipment often used for gamma radiation sterilization of products for medical applications. In some embodiments, such equipment may be used to cure, or partially cure adhesive compositions of the present disclosure. In some embodiments, such curing may occur simultaneously with a sterilization process for a semi-finished or finished product, for example a tape or wound dressing.

Advantageously, crosslinking the silicone gel by radiation with E-beam or gamma radiation avoids any need for additional catalyst materials. In this way, fewer extractable materials remain in the crosslinked poly(diorganosiloxane), including for example any catalytic materials that may have associated toxicity or skin irritation properties. Preferably, the silicone gel is crosslinked in the absence of a peroxide, condensation catalyst, or hydrosilation catalyst. The silicone gel can be substantially free of "—SiH" groups ("substantially free" here refers to less than 0.5 mol % of —SiH groups being present in the silicone gel).

By performing the crosslinking with the hydrophilic component already dispersed in a silicone gel precursor, the hydrophilic component can have a low level of extractability. For example, in some embodiments less than 10 weight percent of the hydrophilic component is extractable into a phosphate buffer saline solution at pH 7 within 24 hours at room temperature. Without being bound by theory, it is thought that at least some portion of the hydrophilic component may be covalently crosslinked to the poly(diorganosiloxane) during E-beam or gamma radiation, making at least that portion of the hydrophilic component less extractable (or even non-extractable).

In some embodiments, less than 9 weight percent, less than 8 weight percent, less than 7 weight percent, less than 6 weight percent, less than 5 weight percent, less than 4 weight percent, less than 3 weight percent, less than 2 weight percent, or even less than 1 weight percent of the hydrophilic component is extractable into a phosphate buffer saline solution at pH 7 within 24 hours at room temperature.

The antimicrobial properties of the adhesive compositions of the present disclosure surprisingly can include a synergistic effect. Adhesive compositions including both the hydrophilic component and the antimicrobial component in a crosslinked poly(diorganosiloxane), where the crosslinking was done by radiation (e.g., E-beam radiation) showed unexpected improvement in antimicrobial properties over comparative compositions lacking the hydrophilic additive.

In some embodiments, adhesive compositions of the present disclosure are suitable for forming articles having medical utility, such as tapes, wound dressings, surgical drapes, IV site dressings, a prosthesis, an ostomy or stoma pouch, a buccal patch, or a transdermal patch. In some embodiments, the adhesives may also be useful for other articles including dentures and hairpieces.

In some embodiments, the adhesive compositions of the present disclosure are suitable for adhering an article to a biological substrate (e.g., a human or an animal). For example, in some embodiments, adhesive compositions of the present disclosure may be used to adhere an article (e.g., a wound dressing) to the skin of humans or animals.

Exemplary substrates include polymeric materials, plastics, natural macromolecular materials (e.g., collagen, wood, cork, and leather), paper, cloth, metals, glass, ceramics, and composites. In some embodiments, the substrate is suitable for making an article suitable for use as a wound dressing. In some preferred embodiments, the substrate comprises at least one of paper, polymeric film, and woven cloth and non-woven cloth. In some embodiments, the substrate can be in the form of a fiber (e.g., a sodium carboxymethylcellulose fiber) or a rope.

The thickness of the adhesive layer is not particularly limited. In some embodiments, the thickness will be at least 10 micrometers, and in some embodiments, at least 20 micrometers. In some embodiments, the thickness will be no greater than 400 micrometers, and in some embodiments, no greater than 200 micrometers.

The peel adhesion to surfaces such as human skin is known to be highly variable. Skin type, location on the body, and other factors can affect results. Generally, average values of peel adhesion from skin are subject to large standard deviations. In some embodiments, the average peel adhesion for human skin may be less than 200 grams/2.54 cm, and in some embodiments, less than 100 grams/2.54 cm.

Exemplary article 100 is illustrated in FIG. 1. Article 100 comprises silicone adhesive 130 associated with a first major surface of substrate 120. Although not shown, in some embodiments, the opposite surface of silicone adhesive 130 may be protected by a release liner. In some embodiments, article 100 may be self-wound, and the opposite (exposed) surface of the adhesive will come into contact with the uncoated major surface of substrate 120. In some methods of using article 100, the surface of silicone adhesive 130 can applied to a surface of interest (e.g., human skin), adhering substrate 120 to that surface.

EMBODIMENTS

Embodiment 1

An adhesive composition comprising:
a) a silicone gel comprising a crosslinked poly(diorganosiloxane) having terminal groups of formula —O—Si($R^1$)($R^2$)$_2$ wherein $R^1$ is hydroxyl, alkyl, or aryl and each $R^2$ is independently alkyl or aryl;
b) a hydrophilic component dispersed in the silicone gel, wherein the hydrophilic component comprises a carbohydrate having at least 3 hydroxyl groups, a carbohydrate derivative having at least 3 hydroxyl groups, or a combination thereof; and
c) an antimicrobial agent dispersed in the silicone gel, wherein the antimicrobial agent comprises elemental copper, elemental silver, a copper-containing compound, a silver-containing compound, or a combination thereof;

wherein less than 10 weight percent of the hydrophilic component is extractable from the adhesive composition into a phosphate buffer saline solution at pH 7 within 24 hours at room temperature.

Embodiment 2

The adhesive composition of embodiment 1, wherein the silicone gel is crosslinked in the absence of a peroxide, condensation catalyst, or hydrosilation catalyst.

Embodiment 3

The adhesive composition of any one of embodiments 1 or 2, wherein the silicone gel is substantially free of —SiH groups.

Embodiment 4

The adhesive composition of any one of embodiments 1 to 3, wherein the silicone gel is crosslinked using an electron beam or gamma radiation.

Embodiment 5

The adhesive composition of any one of embodiments 1 to 4, wherein the hydrophilic component is a cellulosic material, and wherein the cellulosic material is optionally methoxylated or ethoxylated.

Embodiment 6

The adhesive composition of any one of embodiments 1 to 4, wherein the hydrophilic component is a monosaccharide, reduced monosaccharide, disaccharide, reduced disaccharide, polysaccharide, reduced polysaccharide, methoxylated or ethoxylated derivatives thereof, or combination thereof.

Embodiment 7

The adhesive composition of any one of embodiments 1 to 6, wherein the antimicrobial agent comprises a copper salt, silver salt, or a combination thereof.

Embodiment 8

The adhesive composition of any one of embodiments 1 to 7, wherein the adhesive composition comprises 35 to 95 weight percent silicone gel, 5 to 50 weight percent hydrophilic component, and 0.1 to 20 weight percent antimicrobial agent, wherein each amount is based on a total weight of the adhesive composition.

Embodiment 9

The adhesive composition of any one of embodiments 1 to 8, further comprising a tackifier.

Embodiment 10

The adhesive composition of embodiment 9, wherein the tackifier is a silicate resin. Embodiment 11. The adhesive composition of any one of embodiments 8 to 10, wherein the adhesive composition further comprises 0.1 to 59.9 weight percent of a tackifier, based on a total weight of the adhesive composition.

Embodiment 12

The adhesive composition of any one of embodiments 1 to 11, wherein the poly(diorganosiloxane) comprises a poly (dimethylsiloxane) having —Si(OH)(CH$_3$)$_2$ or —Si(CH$_3$)$_3$ terminal groups.

Embodiment 13

The adhesive composition of any one embodiments 1 to 12, wherein the poly(diorganosiloxane) is according to formula 2:

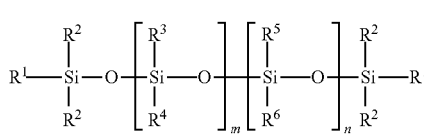

(2)

wherein each R$^1$ is independently hydroxyl, alkyl, or aryl, and wherein each R$^2$, R$^3$, R$^4$, R$^5$, and R$^6$ is independently alkyl or aryl, and m and n are integers, and at least one of m or n is not zero.

Embodiment 14

The adhesive composition according to embodiment 13, wherein one or more of the alkyl or aryl groups contains a halogen substituent.

Embodiment 15

The adhesive composition according to embodiment 14, wherein the halogen is fluorine.

Embodiment 16

An article comprising a substrate and a layer of the adhesive composition according to any one of the preceding embodiments adhered to the substrate.

Embodiment 17

The article of embodiment 16, wherein the layer of the adhesive composition has a thickness of 20 micrometers to 200 micrometers.

Embodiment 18

The article of any one of embodiments 16 or 17, wherein the substrate comprises at least one of paper, polymeric film, and woven cloth and non-woven cloth.

Embodiment 19

A method of adhering a substrate to a biological substrate comprising adhering the adhesive composition according to any one of embodiments 1 to 15 to the substrate, and using the adhesive composition to adhere the substrate to the biological substrate.

Embodiment 20

The method of embodiment 19, wherein the biological substrate is human skin.

EXAMPLES

Electron Beam Ionization Treatment of Samples

Film samples coated with silicone adhesive were exposed to ionizing radiation for crosslinking on an electron beam generating apparatus (obtained from Energy Sciences, Inc., Wilmington, Mass., under the trade designation "MODEL CB-300"). The samples were attached to a polyethylene terephthalate support film to convey them through the nitrogen inerted irradiation chamber of the electron beam generating apparatus.

Absorption Capacity Test Method

The absorption capacity of silicone adhesive samples was determined by the following test method. Triplicate 2.5 centimeter by 2.5 centimeter samples ("initial samples") of polyurethane film coated with silicone adhesive ("initial samples") were weighed, and their masses ("initial weights") were recorded. The samples were placed in a wire mesh basket and loosely covered with a wire mesh to prevent the samples from folding on themselves or sticking to each other. The samples in the wire mesh basket were placed in a jar with 1 liter of phosphate buffer solution (10 mM Na$_2$HPO$_4$) that had been adjusted to pH of 7.4. The samples were kept in the solution after 24 hours, then were removed from the jar and gently blotted to remove surface moisture, and the weighed. Absorption was calculated as the percent increase in mass from the initial mass. These final, weighed samples were then typically evaluated for "Sample Integrity" by measuring extraction of hydrophilic component according to the Sample Integrity Test Method.

Sample Integrity Test Method

"Sample Integrity" (i.e., measurement of extraction of hydrophilic component) was determined by placing the final, weighed samples from the Absorption Capacity Test Method into a pan and drying them for 4 hours at 120° C. The dried samples were then weighed to obtain a weight of dried sample, and the percent weight loss of hydrophilic additive relative to the initial samples (i.e., prior to absorption of phosphate buffer) was calculated using the following equations (where "wt." is an abbreviation for "weight"):

initial wt. of hydrophilic additive = initial wt. percent of hydrophilic additive × initial wt. of sample

Percent weight loss of hydrophilic additive =

$$100 \times \left(1 - \frac{\text{(initial wt. of sample} - \text{wt. of dried sample)}}{\text{initial wt. of hydrophilic additive}}\right)$$

Since the initial samples were each prepared in a total amount of 100 g (i.e., the sum of weights of silicone material, hydrophilic additive, and antimicrobial additive totaled 100 g), the number of grams of hydrophilic additive shown for each of the samples in the Tables below corresponds numerically to the value for initial weight percent of hydrophilic additive.

180° Peel Adhesion Test

The 180° peel adhesion of a silicone adhesive was measured according to ASTM D 3330-90 (Method A). Stainless steel panels were obtained from ChemInstruments, Indian Springs, Ohio. The stainless steel panels were washed sequentially with methylethyl ketone and n-heptane and allowed to dry for 10 minutes prior to use. Silicone adhesive coatings on a polyurethane film having a thickness of 25 micrometers were cut into 2.54 centimeter by 15 centimeter strips. Each strip was then adhered to a 5 centimeter by 20 centimeter clean, solvent-washed stainless steel panel using a 2 kilogram roller passed twice over the strip at 30 centimeters per minute. The bonded assembly dwelled at room temperature for about one minute and was tested for 180° peel adhesion using an IMASS slip/peel tester (obtained from Instrumentors Inc., Strongsville, Ohio under the trade designation "MODEL SP-2000") at a rate of 30 centimeters per minute over a ten second data collection period. Duplicate samples were tested, and the reported peel adhesion value was an average of the peel adhesion values from the individual samples.

Antibacterial Activity Test

Antibacterial activity of the silicone adhesives was evaluated according to JIS Z 2801 (Japan Industrial Standards, Japanese Standards Association, Tokyo, JP). A bacterial inoculum was prepared to a concentration of approximately $1 \times 10^6$ colony forming units per mL in a solution of 1 part Trypticase Soy Broth (BBL Prepared Plated Media, Becton, Dickinson and Company, Sparks, Md.) and 499 parts phosphate buffer (0.3 mM $KH_2PO_4$). Samples were cut as 1 inch by 1 inch (2.54 cm by 2.54 cm) squares. A 150 microliters aliquot of the bacterial suspension was placed onto the surface of the sample and the inoculated sample was incubated for the specified contact time at 27° C.±1° C. After the incubation, the sample was placed into 20 mL of Dey/Engley (D/E) Neutralizing Broth (DIFCO, Becton, Dickinson and Company, Sparks, Md.). The number of surviving bacteria in the Neutralizing Broth was determined by serially diluting and plating on AEROBIC COUNT (AC) PETRIFILM (3M Company, St. Paul, Minn.). The plates were incubated for 48 hours at 35° C.±1° C. Bacterial colonies from appropriate dilution were counted according to the manufacturer's instructions and a Viable Cell Count was recorded as colony-forming units (CFU) per $cm^2$.

Materials

BELSIL TMS-803 (31 grams) were added to a cup and blended for 90 seconds at 2500 rpm in a mixer (obtained from FlackTek Inc, Landrum, S.C., under the trade designation "SPEEDMIXER MODEL DAC 150.1 FV") to form a homogenous solution. The solution was coated at a thickness of 125 micrometers onto a 25 micrometer polyurethane film. The coating was irradiated with an E-beam dose of 7.5 Mrads at 280 keV.

Comparative Example 2 (CE2)

This comparative example illustrated the preparation of a silicone adhesive without hydrophilic or antimicrobial additives for comparison purposes. OHX-4070 (90 grams) and BELSIL TMS-803 (10 grams) were added to a cup and blended for 90 seconds at 2500 rpm in a mixer (obtained from FlackTek Inc, Landrum, S.C., under the trade designation "SPEEDMIXER MODEL DAC 150.1 FV") to form a homogenous solution. The solution was coated at a thickness of 125 micrometers onto a 25 micrometer polyurethane film. The coating was irradiated with an E-beam dose of 7.5 Mrads at 280 keV.

Example 1 (Ex. 1)

A silicone composition of 50.4 grams of OHX-4070 and 22.6 grams of BELSIL TMS-803 were added to a cup and blended for 90 seconds at 2500 rpm in a mixer (SPEEDMIXER MODEL DAC 150.1 FV) to form a homogenous solution. To this solution 12 grams of CMC, 15 grams of CMS, and 2 grams of silver acetate were then added and the cup was mixed again for 90 seconds at 2500 rpm. The solution was coated at a thickness of 125 micrometers onto a 25 micrometer polyurethane film. The coating was irradiated with an E-beam dose of 7.5 Mrads at 280 keV.

| Abbreviation | Description |
| --- | --- |
| AK 60000 | A trimethylsilyl-terminated poly(dimethylsiloxane) silicone fluid, obtained from Wacker Chemical Corp., Adrian, MI, under the trade designation "AK 60000" |
| BELSIL TMS-803 | An MQ silicate resin, obtained from Wacker Chemical Corp., Adrian, MI, under the trade designation "BELSIL TMS-803" |
| CMC | Carboxymethylcellulose ("CMC") obtained from from AMTEX, Lombard, IL, under the trade designation "GELYCEL" |
| CMS | Croscarmellose sodium ("CMS"), an internally crosslinked version of CMC, obtained from FMC Biopolymer Newark, DE, under the trade designation "SD711" |
| D-Mannitol | D-Mannitol obtained from Alfa Aesar, Ward Hill, MA |
| MG 7-9900 | A two-part soft skin adhesive, the two components obtained from Dow Corning, Midland, MI, under the trade designations "DOW CORNING MG 7-9900A" and "DOW CORNING MG 7-9900B" |
| OHX-4070 | A poly(diorganosiloxane) fluid with silanol end groups, obtained from Xiameter, Midland, MI, under the trade designation "OHX-4070" |
| PEG 3400 | Polyethylene glycol, MW 3400 g/mol, Aldrich Chemical Company, Milwaukee, WI |
| Polyurethane film | A 25 micrometer polyurethane film produced by extrusion coating on a polyethylene coated paper, obtained from Bayer Material Science, Pittsburg, PA, under the trade designation "TEXIN 1209" |
| SCOTCHPAK 9741 | Scotchpak 9741 a release liner, obtained from 3M, St. Paul, MN, under the trade designation "SCOTCHPAK 9741" |
| Silver Acetate | Silver acetate, anhydrous 99%, obtained from Alfa Aesar, Ward Hill, MA |

Comparative Example 1 (CE1)

This comparative example illustrated the preparation of a silicone adhesive without hydrophilic or antimicrobial additives for comparison purposes. OHX-4070 (69 grams) and Example 2 (Ex. 2)

A silicone composition of 48.3 grams of OHX-4070 and 21.7 grams of BELSIL TMS-803 were added to a cup and blended for 90 seconds at 2500 rpm in a mixer (SPEED- MIXER MODEL DAC 150.1 FV) to form a homogenous solution. To this solution 30 grams of CMC and 2 grams of silver acetate were then added and the cup was mixed again for 90 seconds at 2500 rpm. The solution was coated 125 micrometers on a 25 micrometer polyurethane film. The coating was irradiated with an E-beam dose of 7.5 Mrads at 280 keV. Adhesion, Absorption and Integrity measurements were performed and results reported in Table 2.

Example 3 (Ex. 3)

A silicone composition of 79.6 grams of OHX-4070 and 8.8 grams of BELSIL TMS-803 were added to a cup and blended for 90 seconds at 2500 rpm in a mixer (SPEED-MIXER MODEL DAC 150.1 FV) to form a homogenous solution. To this solution 8.8 grams of CMC and 2.7 grams of silver acetate were then added and the cup was mixed again for 90 seconds at 2500 rpm. The solution was coated 125 micrometers on a 25 micrometer polyurethane film. The coating was irradiated with an E-beam dose of 7.5 Mrads at 280 keV.

Example 4 (Ex. 4)

A silicone composition of 67.4 grams of OHX-4070 and 7.5 grams of BELSIL TMS-803 were added to a cup and blended for 90 seconds at 2500 rpm in a mixer (SPEED-MIXER MODEL DAC 150.1 FV) to form a homogenous solution. To this solution 22.5 grams of CMC and 2.7 grams of silver acetate were then added and the cup was mixed again for 90 seconds at 2500 rpm. The solution was coated 125 micrometers on a 25 micrometer polyurethane film. The coating was irradiated with an E-beam dose of 7.5 Mrads at 280 keV.

Example 5 (Ex. 5)

A silicone composition of 48.3 grams of OHX-4070 and 21.7 grams of BELSIL TMS-803 were added to a cup and blended for 90 seconds at 2500 rpm in a mixer (SPEED-MIXER MODEL DAC 150.1 FV) to form a homogenous solution. To this solution 30 grams of D-Mannitol and 2 grams of silver acetate were then added and the cup was mixed again for 90 seconds at 2500 rpm. The solution was coated 125 micrometers on a 25 micrometer polyurethane film. The coating was irradiated with an E-beam dose of 7.5 Mrads at 280 keV.

Example 6 (Ex. 6)

A silicone composition of 48.3 grams of AK60000 and 21.7 grams of BELSIL TMS-803 were added to a cup and blended for 90 seconds at 2500 rpm in a mixer (SPEED-MIXER MODEL DAC 150.1 FV) to form a homogenous solution. To this solution 30 grams of CMC and 2 grams of silver acetate were then added and the cup was mixed again for 90 seconds at 2500 rpm. The solution was coated 125 micrometers on a 25 micrometer polyurethane film. The coating was irradiated with an E-beam dose of 7.5 Mrads at 280 keV.

Comparative Example 3 (CE3)

This comparative example illustrated the preparation of a silicone adhesive composition with non-saccharide based hydrophilic additive and an antimicrobial additive for comparison purposes. OHX-4070 (48.3 grams) and BELSIL TMS-803 (21.7 grams) were added to a cup and blended for 90 seconds at 2500 rpm in a mixer (SPEEDMIXER MODEL DAC 150.1 FV) to form a homogenous solution. To this solution 30 grams Polyethylene glycol (PEG 3400) and 2 grams of silver acetate were then added and the cup was mixed again for 90 seconds at 2500 rpm. The solution was coated 125 micrometers on a 25 micrometer polyurethane film. The coating was irradiated with an E-beam dose of 7.5 Mrads at 280 keV.

The materials and amounts used in the preparation of each of the above E-beam treated samples (i.e., Examples 1 to 6 and Comparative Examples 1 to 3) are summarized in Table 1.

TABLE 1

| Sample | Silicone material, grams | | | Hydrophilic additive | Hydrophilic Additive, grams | Silver Acetate, grams |
|---|---|---|---|---|---|---|
| | OHX-4070 | AK 60000 | BELSIL TMS-803 | | | |
| CE1 | 69 | none | 31 | none | none | none |
| CE2 | 90 | none | 10 | none | none | none |
| Ex. 1 | 50.4 | none | 22.6 | CMC, CMS | 12, 15 | 2 |
| Ex. 2 | 48.3 | none | 21.7 | CMC | 30 | 2 |
| Ex. 3 | 79.6 | none | 8.8 | CMC | 8.8 | 2.7 |
| Ex. 4 | 67.4 | none | 7.5 | CMC | 22.5 | 2.7 |
| Ex. 5 | 48.3 | none | 21.7 | D-Mannitol | 30 | 2 |
| Ex. 6 | none | 48.3 | 21.7 | CMC | 30 | 2 |
| CE3 | 48.3 | none | 21.7 | PEG 3400 | 30 | 2 |

180° Peel Adhesion, Absorption Capacity, and Integrity measurements were performed on each of the samples from Table 1, and the results are reported in Table 2.

TABLE 2

| Sample | 180° Peel Adhesion grams per 2.54 cm | Absorption Capacity percent of weight gain | Sample Integrity percent weight loss of hydrophilic additive |
|---|---|---|---|
| CE1 | 232 | 25 | 0 |
| CE2 | 144 | 16 | 1 |
| Ex. 1 | 515 | 107 | 4 |
| Ex. 2 | 284 | 123 | 3 |
| Ex. 3 | 120 | 43 | 2 |
| Ex. 4 | 109 | 81 | 4 |
| Ex. 5 | 199 | 101 | 3 |
| Ex. 6 | 136 | 110 | 2 |
| CE3 | 596 | 65 | 33 |

Comparative Example 4 (CE4)

This comparative example illustrated the preparation of a non-radiation crosslinked silicone adhesive composition. To a SPEEDMIXER cup 50 grams of MG 7-9900 part A and 50 grams of MG 7-9900 part B were added to a cup and blended for 90 seconds at 2500 rpm in a mixer (SPEEDMIXER MODEL DAC 150.1 FV) to form a homogenous solution. The solution was coated 125 micrometers on a 25 micrometer polyurethane film. The coating was heated to 70° C. for 15 minutes to facilitate the crosslinking of the silicone adhesive.

Comparative Example 5 (CE5)

This comparative example illustrated the preparation of a non-radiation crosslinked silicone adhesive composition. To a SPEEDMIXER cup 34 grams of MG 7-9900 part A and 34 grams of MG 7-9900 part B were added to a cup and blended for 90 seconds at 2500 rpm in a mixer (SPEEDMIXER MODEL DAC 150.1 FV) to form a homogenous solution. To this solution 15 grams of CMC and 15 grams of CMS and 2 grams silver acetate were then added and the cup was mixed again for 90 seconds at 2500 rpm. The solution was coated 125 micrometers on a 25 micrometer polyurethane film. The coating was heated to 70° C. for 15 minutes to facilitate the crosslinking of the silicone adhesive.

Comparative Example 6 (CE6)

This comparative example illustrated the preparation of a (non-radiation) crosslinked silicone adhesive and non-saccharide hydrophilic additive. To a SPEEDMIXER cup 34 grams of MG 7-9900 part A and 34 grams of MG 7-9900 part B were added to a cup and blended for 90 seconds at 2500 rpm in a mixer (SPEEDMIXER MODEL DAC 150.1 FV) to form a homogenous solution. To this solution 30 grams of PEG 3400 and 2 grams silver acetate were then added and the cup was mixed again for 90 seconds at 2500 rpm. The solution was coated 125 micrometers on a 25 micrometer polyurethane film. The coating was heated to 70° C. for 15 minutes to facilitate the crosslinking of the silicone adhesive.

Comparative Example 7 (CE7)

This comparative example illustrated the preparation of a (non-radiation) crosslinked silicone adhesive composition. To a SPEEDMIXER cup 34 grams of MG 7-9900 part A and 34 grams of MG 7-9900 part B were added to a cup and blended for 90 seconds at 2500 rpm in a mixer (SPEEDMIXER MODEL DAC 150.1 FV) to form a homogenous solution. To this solution 30 grams of D-Mannitol and 2 grams silver acetate were then added and the cup was mixed again for 90 seconds at 2500 rpm. The solution was coated 125 micrometers on a 25 micrometer polyurethane film. The coating was heated to 70° C. for 15 minutes to facilitate the crosslinking of the silicone adhesive.

The materials and amounts used in the preparation of each of the above non-radiation crosslinked samples (i.e., Comparative Examples 4 to 7) are summarized in Table 3.

TABLE 3

| Sample | Silicone material, grams | | | Hydrophilic Additive, grams | Silver Acetate, grams |
| --- | --- | --- | --- | --- | --- |
| | MG 7-9900 A | MG 7-9900 B | Hydrophilic additive | | |
| CE4 | 50 | 50 | none | none | 2 |
| CE5 | 34 | 34 | CMC/CMS | 15/15 | 2 |
| CE6 | 34 | 34 | PEG 3400 | 30 | 2 |
| CE7 | 34 | 34 | D-Mannitol | 30 | 2 |

Adhesion, Absorption and Integrity measurements were performed on each of the samples from Table 3, and the results are reported in Table 4.

TABLE 4

| Sample | 180° Peel Adhesion grams per 2.54 cm | Absorption Capacity percent of weight | Sample Integrity percent weight loss of hydrophilic additive |
| --- | --- | --- | --- |
| CE4 | 150 | 26 | 0 |
| CE5 | 25 | 106 | 31 |
| CE6 | 15 | 45 | 72 |
| CE7 | 35 | 85 | 36 |

Example 7

This example illustrated the preparation of a silicone adhesive with an antimicrobial and hydrophilic additive according to the present disclosure. OHX-4070 (47 grams) and BELSIL TMS-803 (21 grams) were added to a cup and blended for 90 seconds at 2500 rpm in a mixer (SPEEDMIXER MODEL DAC 150.1 FV) to form a homogenous solution. To this solution 12 grams of CMC, 15 grams of CMS, and 5 grams silver acetate were then added and the cup was mixed again for 90 seconds at 2500 rpm. The resulting solution was coated at a thickness of 200 micrometers onto a 25 micrometer polyurethane film. The coating was irradiated with an E-beam dose of 7.5 Mrads at 280 keV.

Comparative Example 8 (CE8)

This comparative example illustrated the preparation of a silicone adhesive with hydrophilic additive but no antimicrobial additive. OHX-4070 (50 grams) and BELSIL TMS-803 (23 grams) were added to a cup and blended for 90 seconds at 2500 rpm in a mixer (SPEEDMIXER MODEL DAC 150.1 FV) to form a homogenous solution. To this solution 12 grams of CMC and 15 grams of CMS were then added and the cup was mixed again for 90 seconds at 2500 rpm. The resulting solution was coated at a thickness of 200 micrometers onto a 25 micrometer polyurethane film. The coating was irradiated with an E-beam dose of 7.5 Mrads at 280 keV.

Comparative Example 9 (CE9)

This comparative example illustrated the preparation of a silicone adhesive with an antimicrobial additive but no hydrophilic additive. OHX-4070 (66 grams) and BELSIL TMS-803 (29 grams) were added to a cup and blended for 90 seconds at 2500 rpm in a mixer (SPEEDMIXER MODEL DAC 150.1 FV) to form a homogenous solution. To this solution 5 grams silver acetate were then added and the cup was mixed again for 90 seconds at 2500 rpm. The resulting solution was coated at a thickness of 200 micrometers onto a 25 micrometer polyurethane film. The coating was irradiated with an E-beam dose of 7.5 Mrads at 280 keV.

Comparative Example 10 (CE10)

This comparative example illustrated the preparation of a silicone adhesive with an antimicrobial additive but no hydrophilic additive. OHX-4070 (81.8 grams) and BELSIL TMS-803 (9.1 grams) were added to a cup and blended for 90 seconds at 2500 rpm in a mixer (SPEEDMIXER MODEL DAC 150.1 FV) to form a homogenous solution. To this solution 9.1 grams CMC were then added and the cup was mixed again for 90 seconds at 2500 rpm. The resulting solution was coated at a thickness of 200 micrometers onto a 25 micrometer polyurethane film. The coating was irradiated with an E-beam dose of 7.5 Mrads at 280 keV.

Comparative Example 11 (CE11)

This comparative example illustrated the preparation of a silicone adhesive with an antimicrobial additive but no hydrophilic additive. OHX-4070 (69.2 grams) and BELSIL TMS-803 (7.7 grams) were added to a cup and blended for 90 seconds at 2500 rpm in a mixer (SPEEDMIXER MODEL DAC 150.1 FV) to form a homogenous solution. To this solution 23.1 grams CMC were then added and the cup was mixed again for 90 seconds at 2500 rpm. The resulting solution was coated at a thickness of 200 micrometers onto a 25 micrometer polyurethane film. The coating was irradiated with an E-beam dose of 7.5 Mrads at 280 keV.

The materials and amounts used in the preparation of each of the above E-beam treated samples (i.e., Example 7 and Comparative Examples 8 to 11) are summarized in Table 5.

TABLE 5

| Sample | Silicone material, grams | | | Hydrophilic Additive, grams | Silver acetate, grams |
| --- | --- | --- | --- | --- | --- |
| | OHX-4070 | BELSIL TMS-803 | Hydrophilic Additive | | |
| Ex. 7 | 47 | 21 | CMC/CMS | 12/15 | 5 |
| CE8 | 50 | 23 | CMC/CMS | 12/15 | none |
| CE9 | 66 | 29 | none | none | 5 |
| CE10 | 81.8 | 9.1 | CMC | 9.1 | none |
| CE11 | 69.2 | 7.7 | CMC | 23.1 | none |

Antimicrobial activity measurements were performed for the Examples and Comparative Examples listed in Table 6, with results as summarized in Table 6.

TABLE 6

| | S. aureus ATCC 6538 | | P. aeruginosa ATCC 9027 | |
| --- | --- | --- | --- | --- |
| Sample | Viable Cell Count (log CFU/cm2), 24 hours | log reduction ($\log_{10}$), 24 hours | Viable Cell Count (log CFU/cm2), 24 hours | log reduction ($\log_{10}$), 24 hours |
| Ex. 3 | 5.64 | 4.85 | 3.0 | 3.73 |
| Ex. 4 | 5.64 | 4.76 | 1.03 | 5.7 |
| Ex. 7 | 5.51 | 3.35 | 1.63 | 4.07 |
| CE1 | 5.47 | −0.28 | 6.5 | −0.73 |
| CE2 | 5.64 | 0.95 | 6.71 | 0.02 |
| CE8 | 5.51 | 0.12 | 3.65 | 2.05 |
| CE9 | 5.47 | 1.42 | 3.86 | 1.91 |
| CE10 | 5.64 | 0.95 | 6.71 | 0.02 |
| CE11 | 5.64 | −0.29 | 6.61 | 0.12 |

The tests and test results described above are intended solely to be illustrative, rather than predictive, and variations in the testing procedure can be expected to yield different results. All quantitative values in the Examples section are understood to be approximate in view of the commonly known tolerances involved in the procedures used. The foregoing detailed description and examples have been given for clarity of understanding only. No unnecessary limitations are to be understood therefrom.

What is claimed is:

1. An adhesive composition comprising:
   a) 35 to 95 weight percent of a silicone gel based on a total weight of the adhesive composition, the silicone gel comprising a crosslinked poly(diorganosiloxane) having terminal groups of formula O—Si($R^1$)($R^2$)$_2$ wherein $R^1$ is hydroxyl, alkyl, or aryl and each $R^2$ is independently alkyl or aryl;
   b) 5 to 50 weight percent of a hydrophilic component based on the total weight of the adhesive composition, the hydrophilic component being dispersed in the silicone gel, wherein the hydrophilic component comprises a carbohydrate having at least 3 hydroxyl groups, a carbohydrate derivative having at least 3 hydroxyl groups, or a combination thereof and wherein the hydrophilic component is covalently crosslinked to the poly(diorganosiloxane) by electron beam or gamma ray radiation; and
   c) 0.1 to 20 weight percent of an antimicrobial agent based on the total weight of the adhesive composition, the antimicrobial agent being dispersed in the silicone gel, wherein the antimicrobial agent comprises elemental copper, elemental silver, a silver-containing compound, or a combination thereof;

wherein less than 10 weight percent of the hydrophilic component is extractable from the adhesive composition into a phosphate buffer saline solution at pH 7 within 24 hours at room temperature and wherein the adhesive composition is a pressure sensitive adhesive.

2. The adhesive composition of claim 1, wherein the silicone gel is crosslinked in the absence of a peroxide, condensation catalyst, or hydrosilation catalyst.

3. The adhesive composition of claim 1, wherein the silicone gel is substantially free of —SiH groups.

4. The adhesive composition of claim 1, wherein the silicone gel is crosslinked using an electron beam.

5. The adhesive composition of claim 1, wherein the hydrophilic component is a cellulosic material, and wherein the cellulosic material is optionally methoxylated or ethoxylated.

6. The adhesive composition of claim 1, wherein the hydrophilic component is a monosaccharide, reduced monosaccharide, disaccharide, reduced disaccharide, polysaccharide, reduced polysaccharide, methoxylated or ethoxylated derivatives thereof, or combination thereof.

7. The adhesive composition of claim 1, wherein the antimicrobial agent comprises a copper salt, silver salt, or a combination thereof.

8. The adhesive composition of claim 1, wherein the adhesive composition comprises 40 to 80 weight percent silicone gel, 10 to 40 weight percent hydrophilic component, 0.5 to 10 weight percent antimicrobial agent, and 5 to 49.5 weight percent tackifier, wherein each amount is based on a total weight of the adhesive composition.

9. The adhesive composition of claim 1, further comprising a tackifier.

10. The adhesive composition of claim 9, wherein the tackifier is a silicate resin.

11. The adhesive composition of claim 1, wherein the adhesive composition further comprises 0.1 to 59.9 weight percent of a tackifier, based on a total weight of the adhesive composition.

12. The adhesive composition of claim 1, wherein the poly(diorganosiloxane) comprises a poly(dimethylsiloxane) having —Si(OH)(CH$_3$)$_2$ or —Si(CH$_3$)$_3$ terminal groups.

13. The adhesive composition of claim 1, wherein the poly(diorganosiloxane) is of formula 2:

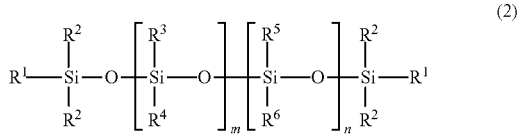 (2)

wherein each $R^1$ is independently hydroxyl, alkyl, or aryl, and wherein each $R^2$, $R^3$, $R^4$, $R^5$, and $R^6$ is independently alkyl or aryl, and m and n are integers, and at least one of m or n is not zero.

14. An article comprising a substrate and a layer of the adhesive composition of claim 1 adhered to the substrate.

15. The article of claim 14, wherein the layer of the adhesive composition has a thickness of 20 micrometers to 200 micrometers.

16. The article of claim 14, wherein the substrate comprises at least one of paper, polymeric film, and woven cloth and non-woven cloth.

17. The adhesive composition of claim 1, wherein the adhesive composition is positioned adjacent to human or animal skin.

18. The adhesive composition of claim 17, wherein the adhesive composition is positioned over a wound site.

19. The article of claim 14, wherein the article is a medical dressing.

20. The adhesive composition of claim 1, wherein the adhesive composition comprises 45 to 60 weight percent silicone gel, 20 to 35 weight percent hydrophilic component, 1 to 5 weight percent antimicrobial agent, and 10 to 34 weight percent tackifier, wherein each amount is based on a total weight of the adhesive composition.

* * * * *

UNITED STATES PATENT AND TRADEMARK OFFICE
CERTIFICATE OF CORRECTION

PATENT NO. : 10,370,571 B2
APPLICATION NO. : 14/648633
DATED : August 6, 2019
INVENTOR(S) : Michael D. Determan It is certified that error appears in the above-identified patent and that said Letters Patent is hereby corrected as shown below:

On the Title Page

Item (54), Title, Delete "HYDROPHILLIC" and insert -- HYDROPHILIC --, therefor.

In the Specification

Column 1
Line 2, Delete "HYDROPHILLIC" and insert -- HYDROPHILIC --, therefor.

Column 5
Line 32, Delete "aliginic" and insert -- alginic --, therefor.

Column 6
Line 48, Delete "$SiO_{412}$" and insert -- $SiO_{4/2}$ --, therefor.

In the Claims

Column 19
Line 67, In Claim 1, delete "O—Si($R^1$)($R^2$)$_2$" and insert -- —O—Si($R^1$)($R^2$)$_2$ --, therefor.

Signed and Sealed this
Twenty-sixth Day of November, 2019

Andrei Iancu
*Director of the United States Patent and Trademark Office*